United States Patent [19]

Warriner

[11] Plant 4,437

[45] Jul. 17, 1979

[54] ROSE PLANT

[75] Inventor: William A. Warriner, Tustin, Calif.

[73] Assignee: Jackson & Perkins Co., Medford, Oreg.

[21] Appl. No.: 920,361

[22] Filed: Jun. 29, 1978

[51] Int. Cl.[2] ..... A01H 5/00

[52] U.S. Cl. ..... Plt./12

[58] Field of Search ..... Plt./12

*Primary Examiner*—Robert E. Bagwill

*Attorney, Agent, or Firm*—Klarquist, Sparkman, Campbell, Leigh, Hall & Whinston

[57] ABSTRACT

A novel grandiflora rose plant characterized by a vigorous, upright growth habit, many cherry and white bicolored flowers with no fragrance, borne in long-stemmed clusters, its many long, abundant thorns, and resistance to mildew and blackspot.

8 Drawing Figures

BACKGROUND OF THE INVENTION

The present invention relates to a new and distinct variety of rose plant of the grandiflora class which was originated by me by crossing an unnamed variety with pollen of the variety Redgold, U.S. Plant Pat. No. 3,006.

The primary objective of this breeding was to produce a new rose variety of the grandiflora class bearing multicolored or bicolored blooms. This objective was substantially achieved as evidenced by the following unique combination of characteristics which are outstanding in the new variety and which distinguish it from its parents as well as from all other varieties of which I am aware:

1. An upright, vigorous plant with a strong tendency to produce blooms in long-stemmed clusters on main canes and small clusters on lateral branches.
2. Flower color essentially cherry red with a white reverse.
3. Little or no fragrance.
4. Very dark Garnette Brown new foliage and stems.
5. Many long, nearly straight thorns.

Asexual reproduction of this new cultivar by budding as performed at Wasco Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color terminology in accordance with Wilson's Horticultural Color Chart, except where ordinary dictionary significance of color is indicated.

Parentage: Seedling.

*Seed Parent.*—Unnamed variety.

*Pollen Parent.*—Redgold, U.S. Plant Pat. No. 3,006.

Classification:

*Botanical.*—Rosa hybrid.

*Commercial.*—Grandiflora.

FLOWER

Observations made from specimens grown at Irvine, Calif., May 1978.

Blooming Habit: Continuous

Bud:

*Size.*—1½ inches when petals start to unfurl.

*Form.*—Pointed ovoid to globular.

*Color.*—When sepals first divide, area immediately under sepals near white. Area exposed near Claret Rose (021). When half blown, upper side of petals similar to, but slightly darker than, Cherry (722); lower side of petals nearly white.

*Sepals.*—Color: Outer surface Garnette Brown (00918/3) with irregular areas of Scheeles Green (860); inner surface same with a light tomentum. Three appendaged sepals lightly appendaged; two unappendaged sepals hairy edged.

*Receptacle.*—Color: Garnette Brown (00918/3); shape: funnel; size: large, broad; surface: smooth.

*Peduncle.*—Length: long; surface: prickly; color: light green to bronzy; strength: stiff, erect, heavy.

*Opening.*—Petals curl back, each becoming pointed.

Bloom:

*Size.*—Large. Average open size 4".

*Stems.*—Long, strong.

*Borne.*—Singly and several together, in clusters which are irregular.

*Form.*—When first open: high center. Permanance: retains its form to the end; outer petal edges slightly curled.

*Petalage.*—Number of petals under normal conditions: 30 to 35.

*Color.*—Center of open flower: upper side of petals near, slightly darker than, Cherry (722). Reverse side of petals near white. Base of petals, upper side: large triangular area of Primrose Yellow (601). Reverse side: large triangular area of Primrose Yellow (601/2). General tonality from a distance — cherry on upper side, with white reverse.

*Variegations.*—Occasional near white streaks.

*Discoloration.*—Third day: slight lightening of cherry color to (722/3).

*Fragrance.*—None.

Petals:

*Texture.*—Thick.

*Shape.*—Round.

*Form.*—Edges slightly quilled.

*Arrangement.*—Imbricated. Petaloids in center, few.

*Persistence.*—Drop off cleanly.

*Lastingness.*—On the plant, long. As cut flower, long.

Reproductive Parts:

*Stamens, anthers.*—Large. Color: yellow. Arrangement: regular around styles.

*Filaments.*—Yellow.

*Pollen.*—Lemon yellow.

*Styles.*—Color: pale yellow, near Primrose Yellow (601/3).

*Stigmas.*—Color: similar to styles.

PLANT

Form: Bush.

Growth: Very vigorous, upright, branching. When growing well, main canes terminate in long-stemmed clusters. Smaller lateral growth generally with one bloom or a few.

Foliage: Number of leaflets on normal mid-stem 5 or 7.

*Size.*—Large.

*Quantity.*—Normal.

*Color.*—New foliage: Garnette Brown (00918); old foliage: Near Spinach Green (0960).

*Shape.*—Oval pointed.

*Texture.*—Leathery.

*Edge.*—Serrated.

*Serration.*—Single, small.

*Petiole.*—Rachis: Color, green; underside, prickles.

*Stipules.*—Long, bearded.

*Disease Resistance.*—Resistant to mildew, blackspot, under normal growing conditions at Irvine, Calif.

Wood:

*New wood.*—Color: bronzy brown. Bark: slightly rough.

*Old wood.*—Color: Green to brown. Bark: slightly rough.

Prickles:

*Quantity.*—On main stalks from base: many. On laterals from stalk: many.

*Form.*—Narrow base, long, straight.

*Color when young.*—Brown.

*Position.*—Irregular.

Small Prickles: None.

I claim:

1. A new and distinct variety of rose plant of the grandiflora class, substantially as shown and described herein, characterized particularly as to novelty by the unique combination of its upright, vigorous growth with many blooms borne in long-stemmed clusters, its cherry and white bicolored flowers with no fragrance, its heavy long, abundant thorns and its dark brown new foliage.

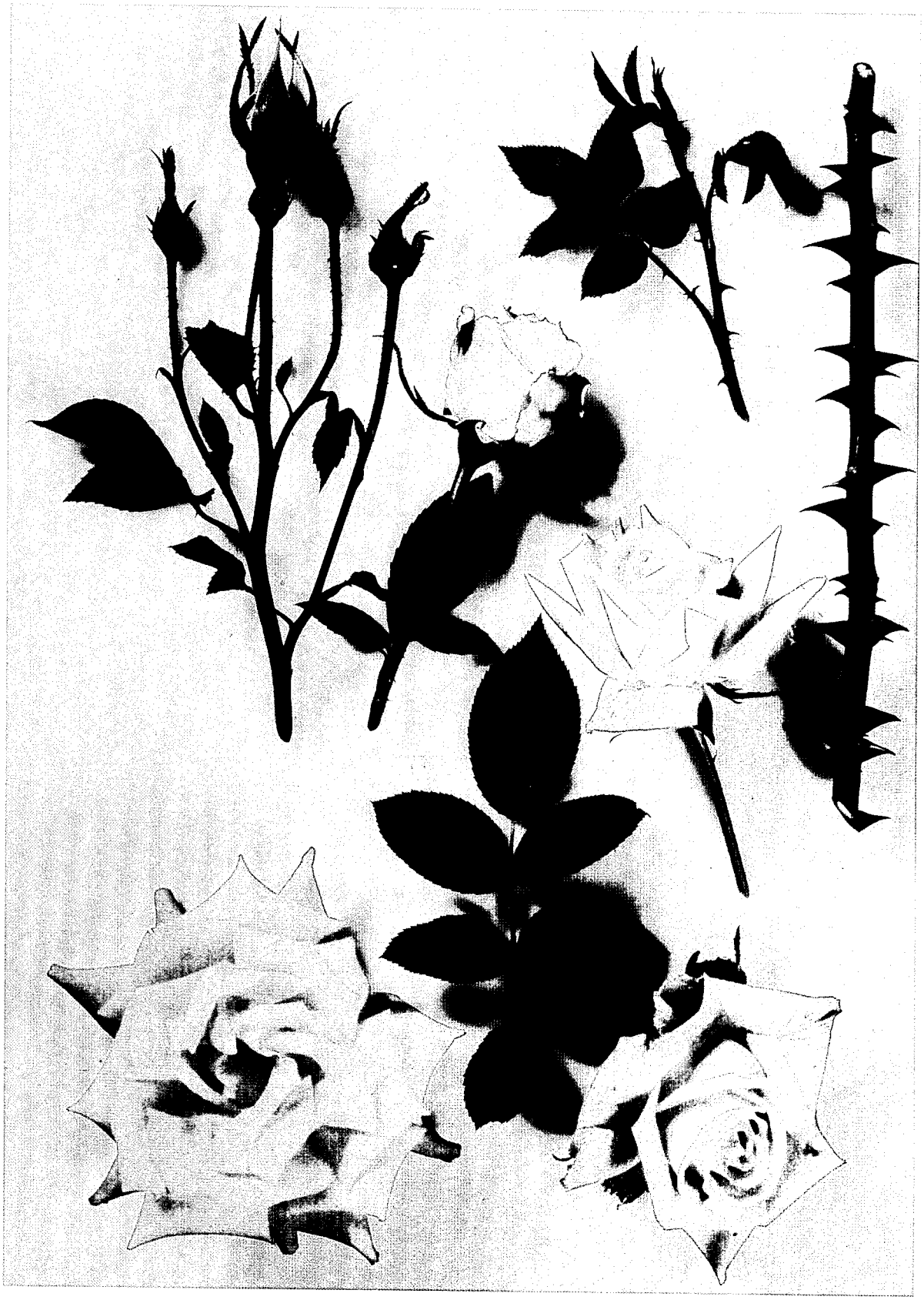

* * * * *